United States Patent [19]

Novak, Jr. et al.

[11] Patent Number: 5,343,543

[45] Date of Patent: Aug. 30, 1994

[54] SIDE-FIRING LASER FIBER WITH DIRECTIONAL INDICATOR AND METHODS OF USE IN DETERMINING THE ORIENTATION OF RADIATION TO BE EMITTED FROM THE SIDE-FIRING LASER FIBER

[75] Inventors: John P. Novak, Jr., San Jose; Barbara A. Eichorn, Campbell, both of Calif.

[73] Assignee: Heraeus Surgical, Inc., Milpitas, Calif.

[21] Appl. No.: 68,245

[22] Filed: May 27, 1993

[51] Int. Cl.$^5$ ............................................. G02B 6/26
[52] U.S. Cl. ...................................... 385/31; 385/77; 385/147; 385/902
[58] Field of Search ................ 372/6; 385/31, 33, 36, 385/76–78, 115, 117, 123, 126, 127, 147, 902

[56] References Cited

U.S. PATENT DOCUMENTS

| | | | |
|---|---|---|---|
| 4,564,736 | 1/1986 | Jones et al. | 385/127 X |
| 4,740,047 | 4/1988 | Abe et al. | 385/31 X |
| 4,985,029 | 1/1991 | Hoshino | 385/31 X |
| 4,986,628 | 1/1991 | Lozhenko et al. | 385/31 |

*Primary Examiner*—John D. Lee
*Attorney, Agent, or Firm*—Workman, Nydegger & Jensen

[57] ABSTRACT

A side-firing laser fiber is provided with a directional indicator for use in determining the orientation of radiation to be emitted from the laser fiber. The laser fiber has an elongate core clad with a nylon jacket. Over a portion of the nylon jacket is placed a sleeve of heat shrinkable material. The sleeve is positioned over the jacket near the distal end of the laser fiber and is heat treated as to be joined to the laser fiber. Biocompatible ink is then applied to the sleeve to form a linear marking capable of delineating the direction of radiation to be emitted from the side-firing laser fiber. In use, the linear marking is oriented in the direction in which the radiation is to be emitted and the laser is then activated. This technique is particularly useful when the distal end of the side-firing laser fiber is obscured from view. The portion of the laser fiber to which the sleeve is attached is still visible when the distal end of the laser fiber is obscured. By utilizing the portion of the linear marking which is still visible, a user can direct the emission of radiation in an advantageous manner.

30 Claims, 3 Drawing Sheets

SIDE-FIRING LASER FIBER WITH DIRECTIONAL INDICATOR AND METHODS OF USE IN DETERMINING THE ORIENTATION OF RADIATION TO BE EMITTED FROM THE SIDE-FIRING LASER FIBER

BACKGROUND

1. Field of the Invention

The present invention relates to the field of surgery. More particularly, the present invention relates to a directional indicator and methods for use in determining the orientation of radiation to be emitted from a side-firing laser fiber utilized in conjunction with an instrument such as an endoscope or laparoscope during examination or surgery.

2. Background Art

Endoscopes, laparoscopes, and other optical examination instruments are utilized to provide visual images to a surgeon regarding the condition of tissue surrounding the distal end of the instrument. The images provided by an examination utilizing one of these instruments can be used to allow surgery utilizing devices incorporated into the instrument or to determine whether more invasive surgery is indicated.

To perform surgery, ancillary devices such as forceps, drills or laser fibers have been incorporated into the endoscopes or laparoscopes By utilizing the visual imaging provided by the endoscope or laparoscope, a surgeon can perform surgery at sites within the body in a manner which is much less invasive than conventional surgery. Even when a naturally occurring orifice is not available to provide access to the surgical area, only a small incision need be created to provide access for a laparoscope.

Another benefit of utilizing endoscopic or laparoscopic examination is that this type of examination or surgery may often be performed using only local anesthesia, resulting in a shorter recovery time for a patient than when utilizing anesthesia which acts upon the central nervous system. In addition, since endoscopic surgery is less invasive, recovery from the surgery is also expedited.

As a result of the benefits of incorporating devices into the endoscope to provide these less-invasive methods for surgery, operations such as gall bladder removal, biopsies, and tumor removal are often accomplished on an outpatient is.

One initial problem encountered when incorporating ancillary devices into the endoscope or laparoscope has been determining the direction at which the forceps or laser fibers are oriented relative to the optical or imaging portion of the endoscope or laparoscope. This is especially important when using side-firing laser fibers wherein the direction of radiation can be emitted at one or more points throughout a 360 degree range. Determining the orientation of radiation to be emitted is especially important since the radiation itself is typically invisible and only the effects of the radiation can be observed.

To assist in the determination of the orientation of the invisible laser beam, a second visible aiming beam, (for example, an HeNe beam) is utilized. The primary, invisible laser beam that does the cutting or removing of tissue is oriented in the identical direction as the visible aiming beam. The physician or surgeon observes the visible nondestructive aiming beam and directs that beam to the desired tissue prior to activating the invisible laser beam.

Another technique utilized to determine the direction of side-firing laser beams is employed in those side-firing laser fibers having a reflector to divert the primary operating beam. In these cases, the orientation of the reflector itself provides the surgeon with the orientation of the side-fired radiation.

Although both the reflector technique and aiming beam technique provide visual feedback to the surgeon regarding the direction of the radiation to be emitted, these techniques are not available when surgery is being performed in tissue which obscures the reflector in the distal tip of the laser fiber or in the case of the aiming beam, when the operating site is overly bloody. Because the aiming beam is commonly an HeNe beam, the beam is red and tends to become difficult to distinguish if the operating site is bloody and thereby has a color similar to the aiming beam.

For example, when an endoscope is advanced into swollen tissue, the distal end of the laser fiber may become obscured from the view provided by the optical portion of the endoscope and the reflector or aiming beam cannot be seen. The direction of the radiation emitted, therefore, is indeterminate.

To overcome these obstacles when performing surgery in swollen tissue wherein the laser fiber is obscured from view and the direction of laser radiation to be emitted is thereby indeterminate, external clocking devices have been developed which are attached externally to the endoscope or laparoscope. These clocking devices are typically aligned with the radiation output of the side-firing laser fiber and are secured in this position to the proximal end of the instrument before the instrument is inserted into the body of the patient.

To utilize a clocking device, the physician diverts his attention from the monitor displaying the operating field (as received from the optical portion of the instrument) to the proximal end of the endoscope. This provides the surgeon with the ability to determine the direction of the radiation even when no observed tissue effect can be ascertained.

In the past, clocking devices have been as simple as attaching the laser fiber to the endoscope or laparoscope. In this permanent relationship the endoscope itself may be used as the clocking device to achieve rotation of the fiber in an ascertainable manner relative to an ascertained starting position. More complex versions of clocking devices utilize a handle attached to the laser fiber with a ratcheting mechanism interrelating with the endoscope to indicate the position of the laser fiber and handle relative to the position of the proximal end of the endoscope.

Use of such clocking devices, however, requires the physician to frequently divert attention from the monitor to the proximal end of the endoscope in order to determine the position of the laser fiber so that the orientation of the radiation to be emitted can be gauged.

A separate problem associated with the use of an endoscope or laparoscope is encountered when a physician attempts to determine the absolute size of anomalous tissues appearing in the viewing area. Absolute measurements are often valuable in order to evaluate the size of a tumor or other tissues to determine whether or not more invasive surgery is indicated. Such absolute measurements are difficult to obtain when viewed through the endoscope as no references are available with which to compare the size of the anomalous tissue.

OBJECTS AND BRIEF SUMMARY OF THE INVENTION

It is, therefore, an object of the present invention to provide a directional indicator and methods of use which provide a surgeon with visual feedback as to the direction of radiation to be emitted from a side-firing laser fiber when the distal end of the laser fiber is obscured from observation.

It is another object of the present invention to provide a directional indicator and methods of use for determining the orientation of radiation to be emitted from a side-firing laser fiber when the laser is used at a bloody operating site.

It is a further object of the present invention to provide a directional indicator and methods of use which allow a surgeon performing an operation to visually determine the direction of radiation emitted from a side-firing laser fiber without diverting the surgeon's vision away from the monitor displaying the field of operation.

It is a still further object of the present invention to provide a directional indicator and methods of use capable of providing an absolute measurement of tissues in the area under consideration.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein a directional indicator and methods of use are provided wherein a side-firing laser fiber having an elongate core clad with a jacket emits laser radiation through an exit site located in the side of the distal end of the elongate core. Affixed to the end of the laser fiber is a cap having a rounded distal end and a truncated proximal end. Located in close proximity to the truncated proximal end of the cap is a sleeve which surrounds a portion of the laser fiber.

In a preferred embodiment of the present invention, the sleeve is comprised of a heat shrinkable material which is heat treated to constrict about the laser fiber and thereby become joined thereto. Printed onto the sleeve is a linear marking which is positioned so as to indicate the location of the exit site of radiation to be emitted from laser fiber. The linear marking is printed on the sleeve utilizing an ink which is of a color providing distinction when present in a bloody environment. In a preferred embodiment of the present invention, the directional indicator comprises a linear marking applied to the sleeve and a portion of the jacket cladding the elongate core.

In use, the laser fiber is attached to a handle or clocking device rotatably affixed to the proximal end of the endoscope. The handle allows manipulation of the fiber in response to the visual image provided on the video monitor of the portion of the laser fiber having the linear marking. The handle employs a tab or fin to give the surgeon a tactile reference point when rotating the fiber clockwise or counterclockwise. When used in conjunction with the linear marking, the surgeon may adjust the orientation of the fiber in small increments while observing that adjustment in the viewing monitor without ever diverting attention away from the viewing monitor. The surgeon's vision is not diverted to the proximal end of the fiber as all visual feedback is provided within the monitor itself. After the endoscope is inserted into the patient, the physician's attention can be focused on the monitor and need not be diverted to ascertain the orientation of the laser fiber.

BRIEF DESCRIPTION OF THE DRAWINGS

In order to more fully understand the manner in which the above-recited and other advantages and objects of the invention are obtained, a more particular description of the preferred embodiments of the present invention briefly described above will be rendered by reference to depictions thereof which are presented in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

As used in this application, the term endoscope is defined to include laparoscopes and other instruments capable of entering the body of a patient and presenting to the user of the instrument an image of the tissue within the patient's body. Tissue imaging is provided through an optical device incorporated into the endoscope to present an image of the tissue surrounding the distal end of the endoscope. The optical device may also be utilized to view the operation of ancillary devices incorporated into the distal end of the endoscope.

The laser fiber has proven to be one of the more beneficial ancillary devices incorporated into endoscopes. The laser fiber allows a physician or surgeon to exploit the non-invasive exploratory advantages of the endoscope by allowing less-invasive laser surgery to be performed by the surgeon from a location remote from the actual surgery.

Figure 1:
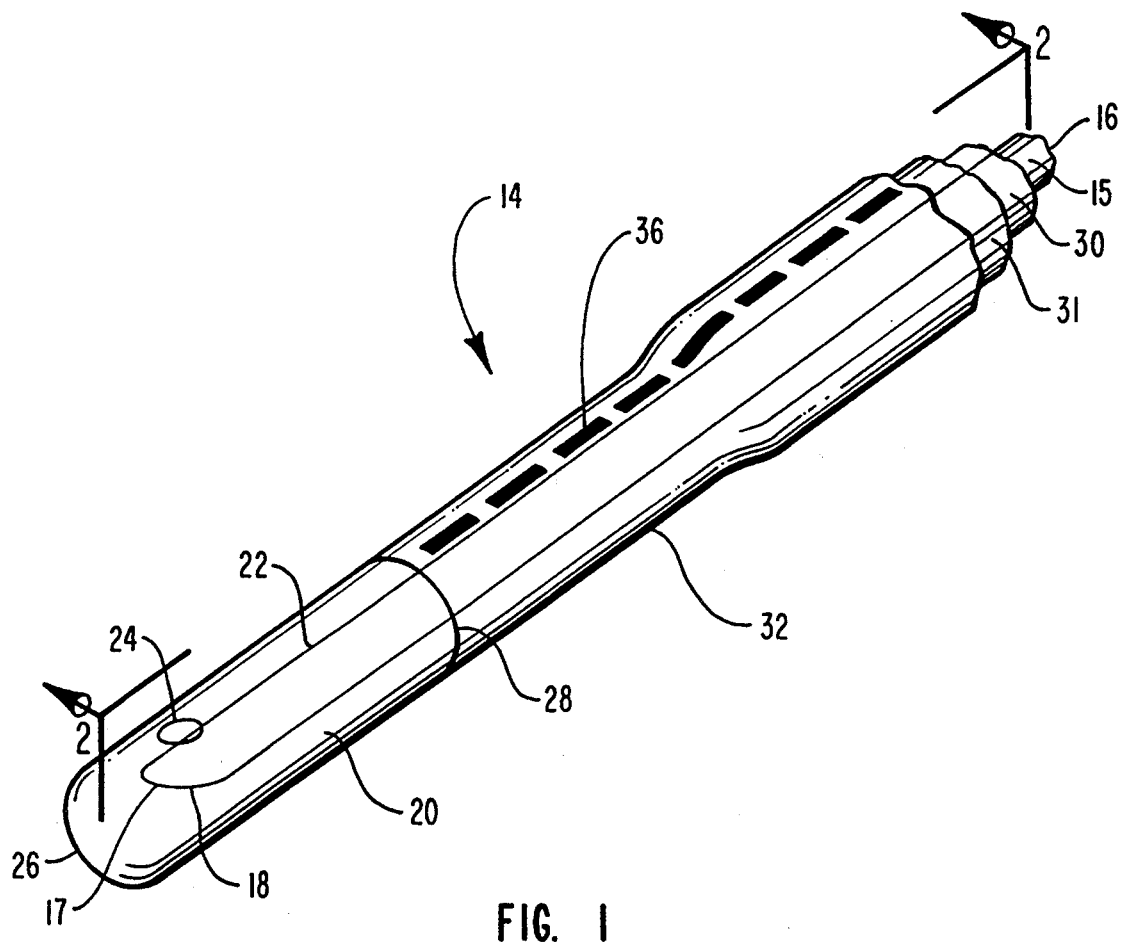
FIG. 1 is a perspective view of a side-firing laser fiber like that used in an endoscope or laparoscope.

Such remote surgery is made possible by extending the laser fiber from the distal end of the endoscope into the viewing area of the optical device. The laser fiber may then be manipulated to remove tissue when activated. Laser fibers utilized to perform this remote surgery emit radiation which is capable of cutting, cauterizing, or vaporizing tissue. The radiation emitted from the laser fiber may be emitted in any direction; however, side-firing laser fibers are often utilized because of the superior control these fibers afford to the physician over the orientation of the radiation emitted therefrom. It has been found easier, for certain orientations and applications, to direct the radiation from a side-firing fiber than from an end-firing fiber. Such a side-firing laser fiber is depicted in FIG. 1.

A side-firing laser fiber 14 is depicted with an elongate core 15 having a proximal end 16 and a distal end 17. The terminus of distal end 17 is tapered so as to provide the angled surface of reflective surface 18 which redirects radiation out the side of fiber 14. Reflective surface 18 serves as a reflector to redirect radiation from a linear orientation along the length of the elongate core to a near perpendicular orientation out the side of the fiber.

Enclosing the distal end 17 of fiber 14 is a cap 20. By way of example, and not limitation, the cap utilized in the presently preferred embodiment illustrated in FIG. 1 is comprised of fused silica. Located in a side 22 of fiber 14 is an exit site 24 through which redirected radiation is emitted. Cap 20 has a rounded distal end 26 and a truncated proximal end 28.

A jacket 30 encloses elongate core 15 for most of the length of fiber 14. Jacket 30 terminates prior to reaching the truncated proximal end 28 of cap 20 to prevent the heat generated by the emission of radiation from damaging the jacket 30. By way of example and not limitation, jacket 30 shown in the embodiment illustrated in FIG. 1 is comprised of polyurethane. Surrounding jacket 30 is a nylon buffer 31. Nylon buffer 31 also terminates prior to reaching proximal end 28 of cap 20. Nylon buffer 31 serves to protect elongate core 15.

A sleeve 32 is formed around that portion of jacket 30 immediately proximal to truncated proximal end 28 of cap 20. Sleeve 32 extends a distance from truncated proximal end 28 in a direction proximal to truncated end 28 along fiber 14 enclosing a portion of nylon buffer 31. By way of example and not limitation, sleeve 32 in one presently preferred embodiment of the instant invention is constructed of heat-shrinkable material and extends approximately four centimeters from truncated proximal end 28. Sleeve 32 is slid over cap 20 and distal end 16 of fiber 14 until the distal end 34 of sleeve 32 is situated close to truncated proximal end 28 of cap 20. Sleeve 32 is then heated and contracted so as to be firmly affixed about the outer surface of fiber jacket 30 and nylon buffer 31. After sleeve 32 has been heat treaters so as to be retained on fiber jacket 30 and nylon buffer 31, sleeve 32 is marked with a linear marking 36 which is used to delineate the position of exit site 24.

Although heat shrinkable material is utilized in the preferred embodiment illustrated in FIG. 1, other methods or materials such as adhesives can be utilized to attach sleeve 32 to jacket 30. Sleeve 32 provides a broad surface on which is printed the linear marking. While this broader surface aids in the marking process, it is not required by the present invention. In some embodiments of the present invention, the linear marking is applied directly to the fiber jacket 30 or nylon buffer 31. The linear marking may also be applied to both the sleeve and a portion of the jacket or buffers. As some embodiments of the present invention do not utilize cap 20, or utilize a cap not having truncated proximal end 28, the linear marking may extend to a point nearer the exit site on these embodiments.

Although many methods may be utilized to apply linear marking 36 to sleeve 32, or even directly to fiber jacket 30 or nylon buffer 31, in the preferred embodiment illustrated in FIG. 1, the linear marking is created by utilizing an image transfer device such as the IMTRAN GS-2400 pad transfer printer or other image transfer device. The image transfer device utilized to apply the linear marking to the presently preferred embodiment has an ink reservoir to which is exposed a cliche having an image of the linear marking engraved therein. A doctor blade scraper is dragged along the surface of the cliche leaving behind the ink in the engraved portion of the cliche but removing the ink on the surface of the cliche. An image transfer pad is then pressed against the cliche to pick up the ink retained by the cliche. This image transfer pad is then pressed against the laser fiber to impart the linear marking thereon.

Although this method is utilized in the presently preferred embodiment of the present invention, many other ink transfer methods may be utilized to impart the linear marking upon the laser fiber.

To assure that the laser fiber is oriented correctly prior to application of the linear marking, when utilizing the inking method currently used in the preparation of the preferred embodiment of the present invention, the laser fiber is energized so that the exit site of the laser energy may be located, and the laser fiber is twisted until the exit site is perpendicular to the jig in which a series of laser of fibers are secured. This assures that the linear marking is within ±5° of the exit site of the radiation.

In the preferred embodiment of the present invention, the ink utilized is green so as to be distinguishable from a bloody background. An example of an ink utilized in the preferred embodiment is a two-part epoxy ink having a hardener which is Ruse 5214 hardener mixed with pad printing ink such as PMS "C" 10-KK or RV-10-KK-Green "C" pad printing ink.

Other methods may be used for creating the linear marking which may be equally applicable to the present invention. One limitation is that the material must be biocompatible and be capable of adhering to the laser fiber. In a presently preferred embodiment of the present invention the linear marking is green so as to contrast with the surrounding tissues and fluids in a bloody operating environment. In choosing a color of ink, it is not only important to choose a color which is easily distinguishable from the bloody operating environment, but it is also important to take into consideration the energy absorption and reflection qualities imparted to the ink by that choice of color.

For example, the darker the color, the more likely for that ink to absorb laser radiation. An ink with a color such as black will absorb too much radiation and become hot to the point where the surrounding tissue will be damaged by the heat emitted from the black ink. The color of ink chosen for use on the preferred embodiment is a green having a lighter tint so as not to absorb an inappropriate amount of laser radiation. Other characteristics may be incorporated into the ink selection such as radiopacity.

The linear marking is applied to the fiber after the sleeve has been reduced in diameter through heat treatment. The benefit derived from applying the linear marking to sleeve 32 subsequent to the shrinking of the sleeve is that the linear marking is not then subjected to the various rates of shrinkage occurring within the sleeve. For example, a linear marking applied to the sleeve prior to shrinkage will not remain linear and thereby obviates any benefits provided by the linear marking in determining the orientation of the radiation emitted from exit site 24 or the scale of the marking will vary due to differences in the shrink rate of sleeve.

The linear marking is typically applied to the sleeve to correspond to the exit site, however, the linear marking in some applications may be applied to the side of the sleeve opposite the exit site. A further embodiment could also comprise a linear marking of one color oriented directly with the exit site and a second linear marking located opposite the exit site of a different color.

Figure 2:
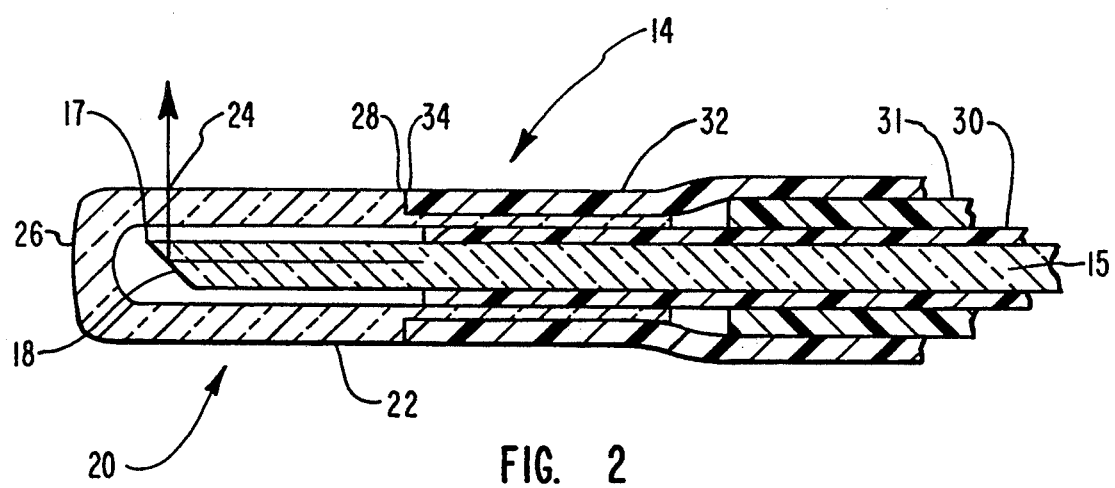
FIG. 2 is a cross-sectional view taken along lines 2-2 in FIG. 1.

FIG. 2 is a cross-sectional view of the laser fiber illustrated in FIG. 1. The present invention is provided with means for redirecting radiation transmitted along the elongate core to a direction substantially perpendicular to the longitudinal axis of the elongate core. By way of example and not limitation, the means for redirecting radiation utilized in the embodiment illustrated in FIG. 2 is reflective surface 18 which redirects radiation which travels along the longitudinal access of core 15 into a more perpendicular orientation to emit radiation through exit site 24. Reflective surface 18 is formed at the terminus of distal end 17. Redirected radiation passes through cap 20 and is utilized to cauterize, cut, or vaporize tissue. In the embodiment illustrated in FIG. 2, jacket 30 terminates prior to abutting truncated proximal end 28 of cap 30, but sleeve 32 is shown in abutment therewith.

Figure 3:
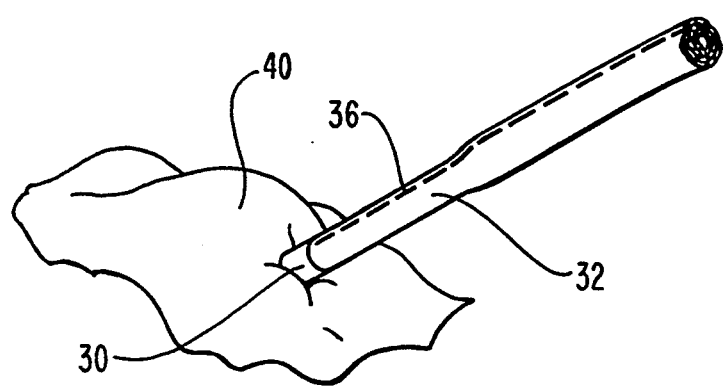
FIG. 3 is an elevational view of a side-firing laser fiber like that illustrated in FIG. 1 shown inserted into swollen tissue.

To more fully appreciate the benefits derived from the instant invention, reference should now be made to FIG. 3 in which laser fiber 14 is shown introduced into an area of swollen tissue 40. Swollen tissue 40 obscures the distal end 17 of fiber 14. When used in this environment, the orientation of emission of radiation from exit site 24 is indeterminate by direct observation.

By utilizing the linear marking of the present invention, such as linear marking 36, however, the orientation of exit site 24 may be determined. By referring to the linear marking on sleeve 32 at a point not obscured by swollen tissue 40, the direction of laser radiation from exit site 24 can be gauged even when exit site 24 is out of the view of the user. The user simply aligns the linear marking with the tissue to be affected and activates the laser. This may all be accomplished without the user diverting his or her attention from the monitor displaying the field of operation. Any adjustments made to the proximal end of the laser fiber are immediately discernable in the monitor thereby providing a very natural aiming technique.

Figure 4:
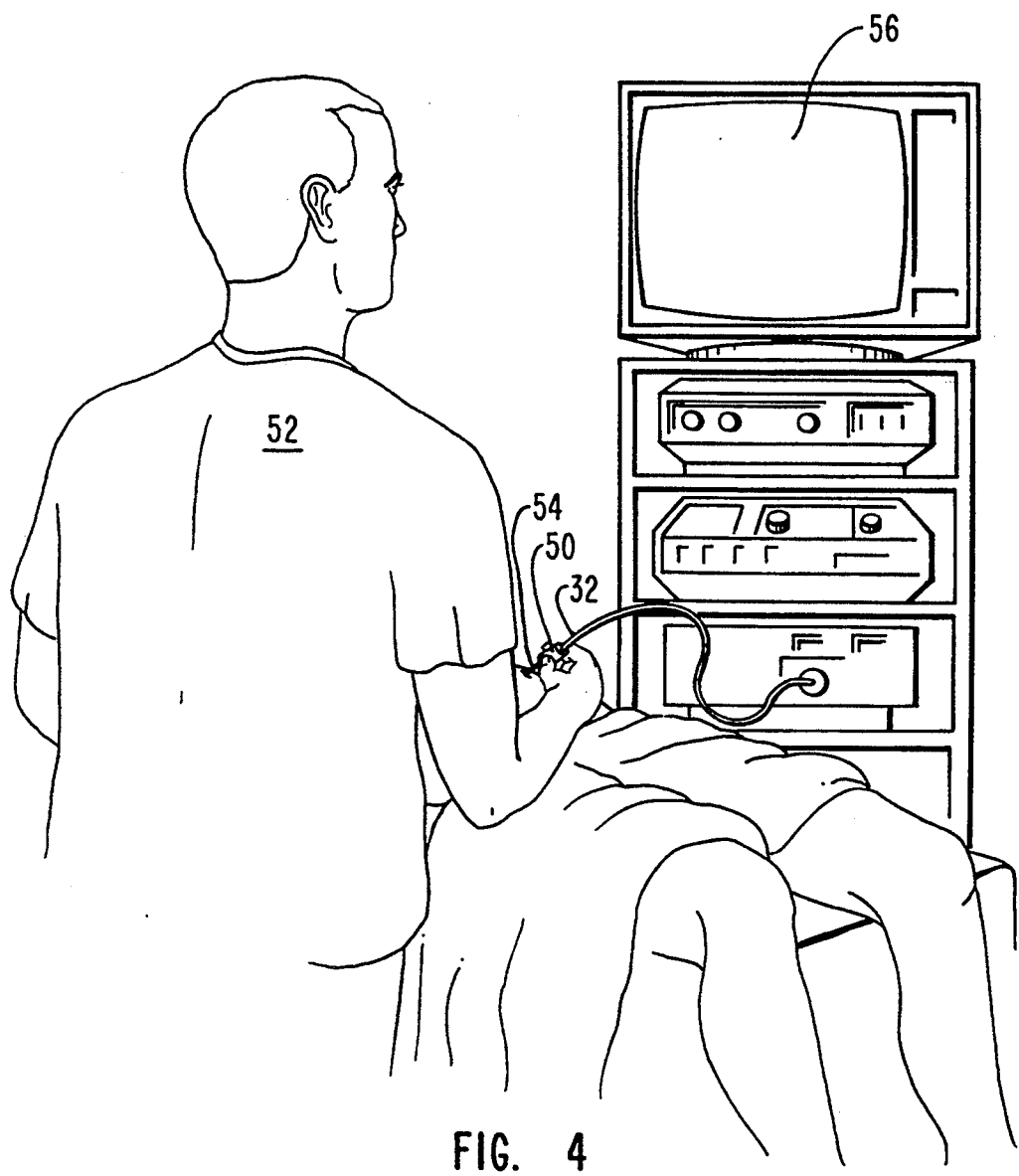
FIG. 4 is a perspective view of the environment in which the present invention is utilized.

To more fully appreciate the advantages provided by this natural aiming technique, reference may now be made to FIG. 4 in which a surgical suite is depicted having illustrated therein a physician performing an operation utilizing an endoscope incorporating the clocking device affixed to the proximal end of a laser fiber.

Clocking devices such as clocking device 50 require that the user 52 of an endoscope 54 divert attention from a viewing monitor 56 down to a proximal end 58 of the endoscope and back up to the viewing monitor. This is distracting and confusing as frequent reference must be made both to the viewing monitor 56 and the proximal end 58 of the endoscope 54.

In contradistinction, one benefit of the present invention is that the orientation of the laser fiber is immediately apparent when viewed through the viewing monitor 56. The user's attention need not be diverted away from the monitor and a much more natural guidance of the laser fiber may be achieved.

Figure 5:
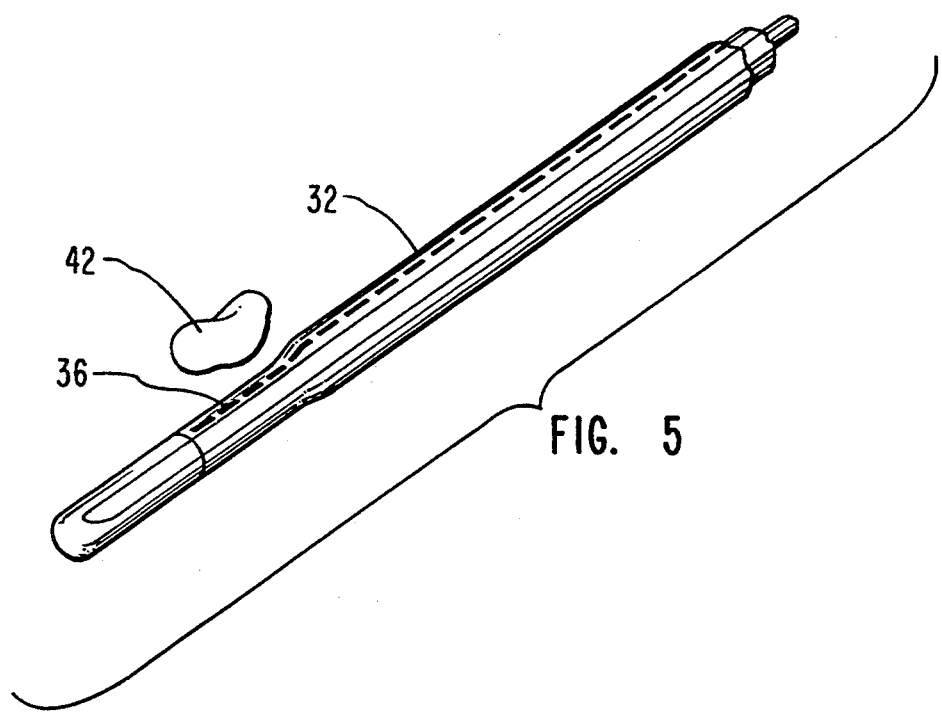
FIG. 5 is a prespective view of a side-firing laser fiber like that illustrated in FIG. 1 placed adjacent to specific tissue to obtain an absolute measurement thereof.

A further benefit derived from the present invention is illustrated in FIG. 5. FIG. 5 depicts laser fiber 14 placed next to a tumor 42. An endoscope is often used as an exploratory instrument to provide a surgeon with a visual image of tissue to assist in determining whether more invasive surgery is indicated. It is often beneficial during these examinations to obtain an absolute measurement of the anomalous tissue being examined. As the view through the imaging device is relative, however, no absolute measurements can be obtained.

By precise application of linear marking 36, however, a measurement system is provided wherein the anomalous tissue can be directly compared to a portion of linear marking 36 on sleeve 32. As the spacing and the length of linear marking 36 are a known factor, sleeve 32 may be placed alongside the anomalous tissue and viewed by the imaging device to obtain an absolute measurement of the anomalous tissue being examined.

For example, it may be determined that the anomalous tissue is four segments long. By printing each segment a precise length and spacing those segments precisely, the size of the tissue may be determined.

This provides invaluable information to the surgeon in determining which type of surgery is indicated.

A surprising advantage of the present invention is realized when performing an operation wherein the laser fiber must be inserted into swollen tissue at a predetermined distance. By utilizing the inventive linear marking, a surgeon can determine how far the fiber is inserted by reference to the portion of the linear marking which remains exposed. For example, if the linear marking is 4 centimeters long and is broken so as to form 20 segments, the surgeon may insert the fiber until only a predetermined number of segments are exposed. This technique may also be utilized when a surgeon wishes to emit radiation at progressive points within the swollen tissue.

By using the linear marking in this manner, a surgeon is provided with visual feedback as to the direction of radiation emitted from the side-firing laser fiber when the distal end of the laser fiber is obscured from observation. As the linear marking is created with an ink of a color which is distinctive in contrast with a bloody operating site, the direction of radiation emitted from the side-firing laser may be determined even in a bloody operating site. By inserting the endoscope and utilizing the directional indicator of the present invention, a surgeon may not only control the direction of radiation emitted from the laser fiber when the distal end of the laser fiber is obscured from vision, but may also determine the depth to which the laser fiber is inserted into the swollen tissue.

This surprising result provides the surgeon with both rotational and linear control over the distal tip of the laser fiber even when that distal tip is totally obscured from vision. By utilizing this technique, a surgeon may also determine the absolute size of anomalous tissue by comparing that tissue to the regular segments of the broken linear marking utilized in a preferred embodiment of the present invention. All of these advantages combine to allow the surgeon to manipulate the laser fiber without ever diverting the surgeon's attention away from the viewing monitor. This provides for a much more natural and controlled manipulation of the laser fiber.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A side-firing laser fiber capable of emitting radiation, the laser fiber comprising:
   a) a laser fiber through which laser radiation is directed, the laser fiber having an emitting tip;
   b) means for redirecting radiation at the emitting tip to a substantially side-firing angle from the longitudinal axis of the laser fiber; and
   c) a linear marking associated with said laser fiber, said linear marking extending a sufficient distance proximally from a position near the emitting tip so as to provide a reference with respect to the direction of radiation emitted from the emitting tip and to be visible even if the emitting tip is not itself visible during use, said linear marking being formed of a plurality of spaced-apart segments so as to permit measurement of the depth of insertion of the laser fiber into tissue and measurements within the surgical site.

2. A side-firing laser fiber as recited in claim 1, wherein the linear marking is comprised of biocompatible ink.

3. A side-firing laser fiber as recited in claim 2, wherein each of the plurality of spaced-apart segments of the linear marking and spaces between said segments are the same length.

4. A side-firing laser fiber as defined in claim 3, wherein the ink is green.

5. A side-firing laser fiber as recited in claim 1, wherein the linear marking is situated in linear alignment with the radiation to be emitted from the emitting tip and extends from a position proximally adjacent to the emitting tip.

6. A side-firing laser fiber as recited in claim 5, wherein each of the plurality of spaced-apart segments of the linear marking and spaces between said segments are the same length.

7. A side-firing laser fiber as recited in claim 1, wherein the linear marking is situated opposite the direction of emission of radiation to be emitted from the emitting tip.

8. A side-firing laser fiber as recited in claim 7, wherein each of the plurality of spaced-apart segments of the linear marking and spaces between said segments are the same length.

9. A side-firing laser fiber as recited in claim 1, wherein each of the plurality of spaced-apart segments of the linear marking and spaces between said segments are the same length.

10. A side-firing laser fiber as recited in claim 1, wherein the means for redirecting radiation comprises a reflective surface formed at the terminus of the distal end of the laser fiber.

11. A side-firing laser fiber as recited in claim 1, wherein the linear marking is green.

12. A side-firing laser fiber as recited in claim 1, wherein the linear marking is radiopaque.

13. A side-firing laser fiber as recited in claim 1, further comprising a sleeve extending proximally from a position proximally adjacent to the emitting tip, and wherein the linear marking is applied to said sleeve.

14. A side-firing laser fiber as recited in claim 13, wherein the linear making is green.

15. A side-firing laser fiber as recited in claim 1, further comprising a sleeve over a portion of the laser fiber near the emitting tip, and wherein the linear marking is applied to said sleeve.

16. A side-firing laser fiber as recited in claim 1, wherein the linear marking is approximately 4 centimeters long.

17. A side-firing laser fiber and directional indicator capable of emitting radiation utilized in performing surgery in conjunction with devices providing visual imaging such as endoscopes and laparoscopes, the side-firing laser fiber comprising;
   a) an elongate core through which laser radiation is directed, the elongate core having a distal tip;
   b) a jacket, the jacket cladding the elongate core along substantially the entire length of the elongate core;
   c) means for redirecting radiation transmitted along the longitudinal axis of the elongate core to a direction substantially side-firing with respect to the longitudinal axis of the elongate core;
   d) a sleeve surrounding a portion of the elongate core, the sleeve having an exterior surface and an interior surface; and
   e) a linear marking visible on the exterior surface of the sleeve, said linear marking extending a sufficient distance proximally from a position near the means for redirecting radiation so as to provide a reference with respect to the direction of radiation emitted from the means for redirecting radiation and to be visible even if the means for redirecting radiation is not itself visible during use, said linear marking being formed of a plurality of spaced-apart segments so as to permit measurement of the depth of insertion of the laser fiber into tissue and measurements within the surgical site.

18. A side-firing laser fiber as recited in claim 17, wherein the sleeve is comprised of heat shrinkable tubing.

19. A side-firing laser fiber as recited in claim 17, wherein the elongate core is comprised of quartz.

20. A side-firing laser fiber as recited in claim 17, wherein each of the plurality of spaced-apart segments of the linear marking and spaces between said segments are the same length.

21. A side-firing laser fiber as recited in claim 17, wherein the linear marking is comprised of nontoxic, inert ink.

22. A side-firing laser fiber as recited in claim 17, wherein the sleeve is heat shrunk to the elongate core.

23. A side-firing laser fiber as recited in claim 17, wherein the linear marking is situated on the sleeve in linear alignment with the direction of radiation to be emitted from the side-firing laser and extends from a position proximally adjacent to the distal tip.

24. A side-firing laser fiber as recited in claim 17, wherein the linear marking is situated opposite the direction of laser radiation to be emitted from the side-firing laser.

25. A side-firing laser fiber as recited in claim 17, wherein the linear marking is green.

26. A side-firing laser fiber as recited in claim 17, wherein the linear marking is approximately 4 centimeters long.

27. A method for determining the direction of radiation emitted from a side-firing laser fiber comprising the steps of:
   a) obtaining a side-firing laser fiber having a linear marking associated with the fiber, the marking corresponding to the direction in which radiation is to be emitted from the fiber, and said marking being formed of a plurality of spaced-apart segments so as to permit measurement of the depth of insertion of the laser fiber into tissue and measurements within the surgical site;

b) inserting the distal end of the laser fiber a known distance into tissue of a patient by observing the portion of the linear marking which remains exposed outside of the tissue;

c) orienting the marking in order to control the direction in which laser radiation is to be emitted; and d) emitting laser radiation.

28. A method for determining the direction of radiation emitted from a side-firing laser fiber as defined in claim 27, wherein the marking associated with the fiber is green.

29. A method for applying a linear marking to a side-firing laser fiber, the method comprising the steps of:

a) positioning a heat shrinkable sleeve over a portion of a side-firing laser fiber;

b) applying heat to the heat shrinkable sleeve to cause the sleeve to become secured to the side-firing laser fiber; and c) applying ink to the sleeve to form a linear marking thereon extending a sufficient distance proximally from a position near an emitting tip of the side-firing laser fiber so as to provide a reference with respect to the direction of radiation to be emitted from the emitting tip and to be visible even if the emitting tip is not itself visible during use, said linear marking being formed of a plurality of spaced-apart segments so as to permit measurement of the depth of insertion of the laser fiber into tissue and measurements within the surgical site.

30. A method for applying a linear marking to a side-firing laser fiber as defined in claim 29, wherein the ink applied to the sleeve to form a linear marking is green.

* * * * *

UNITED STATES PATENT AND TRADEMARK OFFICE
CERTIFICATE OF CORRECTION

PATENT NO. : 5,343,543
DATED : August 30, 1994
INVENTOR(S) : JOHN P. NOVAK, JR. et al.

It is certified that error appears in the above-identified patent and that said Letters Patent is hereby corrected as shown below:

Column 1, line 28, after "laparoscopes" insert --.--
Column 1, line 49, "is" should be --basis--
Column 7, line 46, "surgical suite" should be --surgical site--
Column 10, line 13, after "cladding" insert --of--

Signed and Sealed this

Twelfth Day of December, 1995

*Attest:*

BRUCE LEHMAN

*Attesting Officer*   Commissioner of Patents and Trademarks